Figure 1:
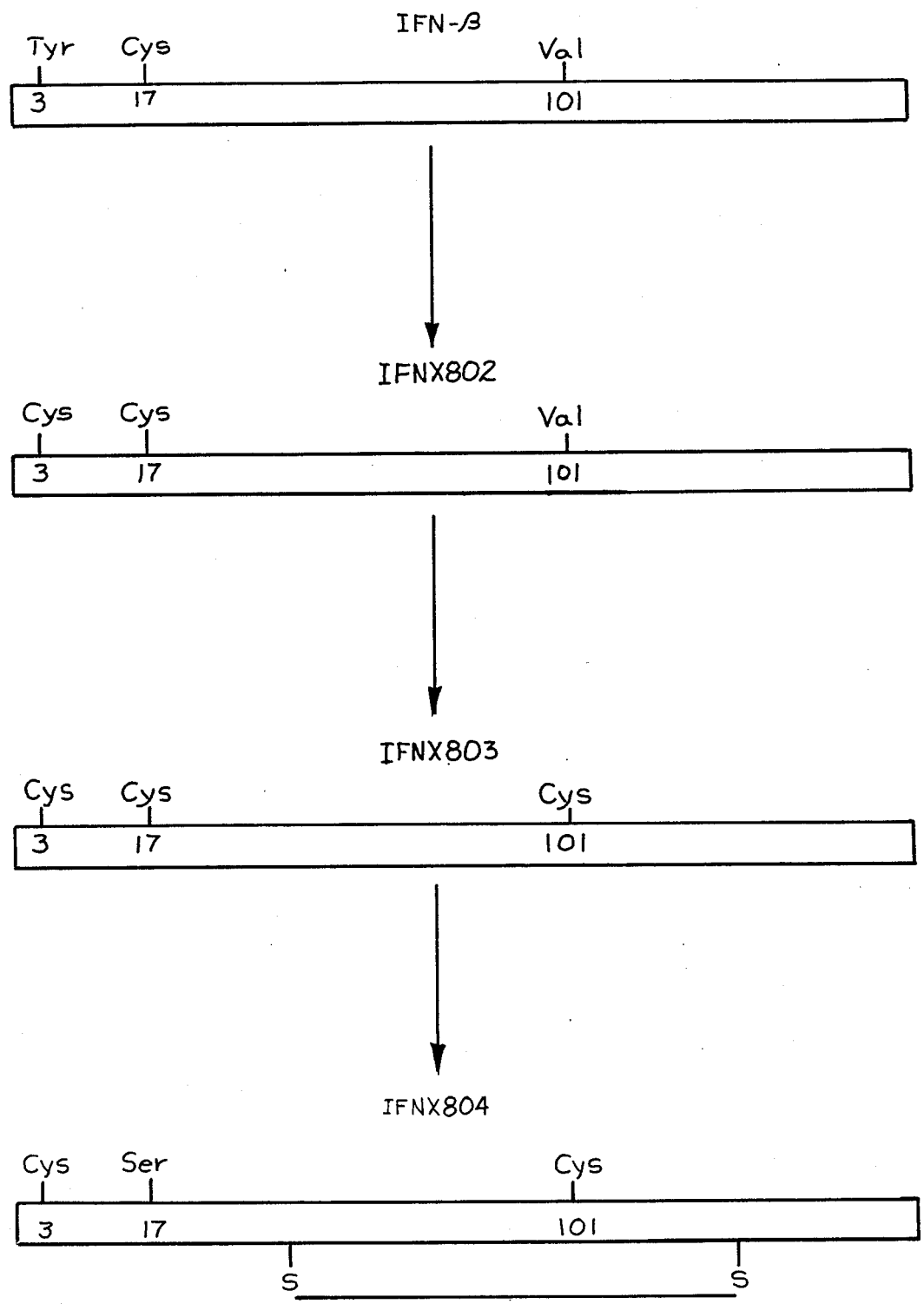

United States Patent [19]

Bell et al.

[11] Patent Number: 4,751,077

[45] Date of Patent: Jun. 14, 1988

[54] INTERFERONS WITH NOVEL CYSTEINE PATTERN

[75] Inventors: Leslie D. Bell, Thame; John C. Smith, High Wycombe; Alan G. Porter, High Wycombe; John R. Adair, High Wycombe, all of United Kingdom

[73] Assignee: G. D. Searle & Co., Chicago, Ill.

[21] Appl. No.: 676,900

[22] Filed: Nov. 30, 1984

[30] Foreign Application Priority Data

Dec. 12, 1983 [GB] United Kingdom ............... 8334102

[51] Int. Cl.$^4$ .................... A61K 45/02; C07K 13/00; C07K 15/26; C12P 21/00

[52] U.S. Cl. .................................. 424/85; 530/351; 435/68; 435/811

[58] Field of Search ............... 424/85; 435/68, 811, 435/172.3; 530/351

[56] References Cited

U.S. PATENT DOCUMENTS 4,414,150 11/1983 Goeddel .......................... 435/172.3
4,569,908 2/1986 Mark et al. ......................... 435/811
4,588,585 5/1986 Mark et al. ........................ 435/68

FOREIGN PATENT DOCUMENTS 0109748 5/1984 European Pat. Off. .

OTHER PUBLICATIONS

Shepard et al., Nature, vol. 294, pp. 563–565, 1981.
Lengyel, Annual Review of Biochemistry, 51:251, 1982.
Wang, A., et al, Science, 224:1431, Jun. 29, 1984.
Thannhauser, T. W., et al, Analytical Biochemistry, 138:181–188, 1984.

Primary Examiner—Blondel Hazel
Attorney, Agent, or Firm—Mary Jo Kanady; Paul D. Matukaitis

[57] ABSTRACT

Human interferons containing novel cysteine substitutions and disulfide bonds are disclosed. The amino acid sequence of a first interferon is combined with the cysteine and/or disulfide pattern of a second interferon resulting in a molecule with hybrid properties.

9 Claims, 7 Drawing Sheets

SITE DIRECTED CHANGES

1. Amino Acid 3. Human IFN-β, Tyr → Cys

Product IFNX802 (HuIFN-β(Tyr$^3$ → Cys$^3$))

|  |  | 1<br>Met | | 3<br>Tyr | 5<br>Asn | Leu |  |
|---|---|---|---|---|---|---|---|
| Original Sequence 5' | TCC | ATG<br>1 | AGC | TAC<br>— | AAC<br>10 | TTG | 3' |
| Primer | 3'G | TAC | TCG | ACG | TTG | A | 5' |
| New Sequence |  | TCC | ATG | AGC | TGC<br>—<br>Cys | AAC | TTG |

FIG. 4

SITE DIRECTED CHANGES

2. Amino Acid 101. Human IFNX802, Val → Cys

Product IFNX803

(HuIFN-β(Tyr$^3$ → Cys$^3$) (Val$^{101}$ → Cys$^{101}$))

|  | 98<br>Leu | Lys | 100<br>Thr | Val | 102<br>Leu | Glu | 104<br>Glu |  |
|---|---|---|---|---|---|---|---|---|
| Original Sequence 5' | CTG | AAG | ACA | GTC | CTG | GAA | GAA | 3' |
| Primer |  | AC | TTC | TGT | ACG | GAC | CTT | C  5' |
| New Sequence | CTG | AAG | ACA | TGC<br>Cys | CTG | GAA | GAA |  |

FIG. 5

SITE DIRECTED CHANGES

3. Amino Acid 17. Human IFNX803 Cys -> Ser

Product IFNX804

(HuIFN-β(Tyr$^3$ -> Cys$^3$)(Val$^{101}$ -> Cys$^{101}$)(Cys$^{17}$ -> Ser$^{17}$))

|  | 13<br>Ser | Asn | 15<br>Phe | Gln | 17<br>Cys | Gln |  |
|---|---|---|---|---|---|---|---|
| Original Sequence 5' | AGC | AAT | TTT | CAG | TGT | CAG | 3' |
| Primer |  G | TTA | AAA | GTC | TCA | GTC | 5' |
| New Sequence | AGC | AAT | TTT | CAG | AGT<br>Ser | CAG |  |

FIG. 6

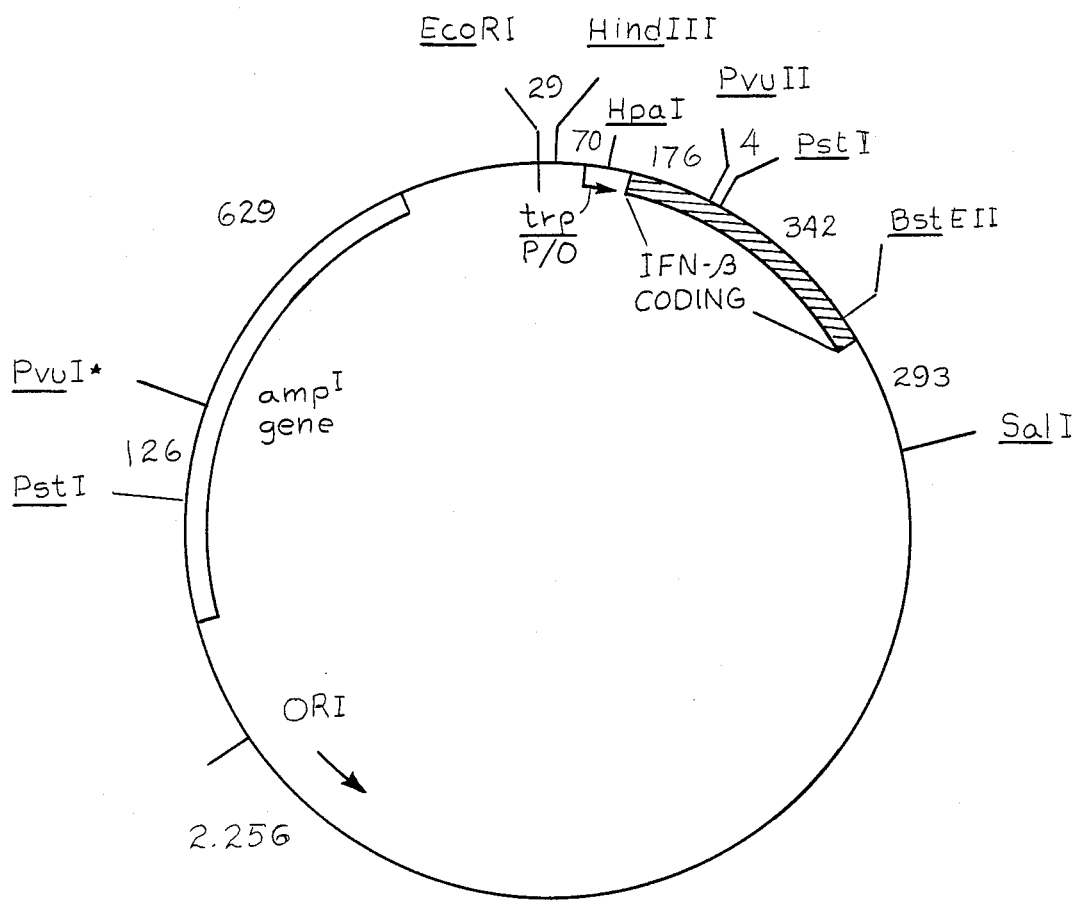

INTERFERONS WITH NOVEL CYSTEINE PATTERN

BACKGROUND OF THE INVENTION

1. Field of the Invention

This invention describes the use of recombinant DNA technology for the design of novel interferon molecules. These novel interferons comprise the amino acid sequence of human beta interferon modified by the addition or deletion of one or more cysteine residues thereby changing the disulfide cross-linking characteristics of the interferon.

2. Description of the Prior Art

INTRODUCTION

The novel feature of the invention described below is that the coding sequence of the human interferon beta gene (HuIFN-β) has been changed at specific points, by the process of site directed mutagenesis, to induce novel amino acid arrangements.

Specifically the number and arrangement of cysteine residues has been altered to produce a pattern analogous to that observed in the human interferon-α (HuIFN-α) family. The novel arrangement is expected to impose an IFN-α-like tertiary structure on the IFN-β protein sequence and hence lead to novel properties of the molecule.

The alpha and beta interferons, specifically Human IFNα$_1$; (D) and Human IFN-β have been shown to be structurally related. They are 45% homologous at the nucleotide level and 29% homologous at the amino acid level (Taniguchi et al., Nature 285 547 (1980). Sternberg and Cohen (Int. J. Biol. Macromol. 4 137 (1982)) have produced a model suggesting the α and β interferons' tertiary structure may be similar. Disulfide bonds are known to influence both tertiary protein structure and stability. The tertiary structure of the Human IFNα has been shown to be in part dependent upon the disulfide linkages (Wetzel et al. UCLA Symp. Mol. Cell Biol. 1982, 25, 365–376).

The interferons are a class of proteins that occur in vertebrates and function as biological regulators of cell function which include increasing resistance to pathogens, limiting cell growth and modulating the immune system. The most studied property of the interferons is their ability to convert cells into an "antiviral" state during which they are more resistant to virus replication (Lengyel, Annual Review of Biochemistry, 51:251,1982).

In addition to conferring antiviral resistance on target cells, interferons (IFNs) have both immunomodulatory and antiproliferative properties (Stewart, 1979, The Interferon System, Springer, Berlin). The IFNs, by virtue of their antigenic, biological and physico-chemical properties, can be grouped into three classes: Type I, IFN-α ("leucocyte") and IFN-β ("fibroblast"); and Type II, IFN-γ ("immune") (Stewart et al., 1980, Nature, 286, 110). Detailed information is now available on the virus-induced, acid stable IFN-α and IFN-β and the mitogen-induced IFN-γ. All three IFN cDNAs have been cloned from their respective induced mRNAs, the DNA sequenced and their potential protein sequences deduced (Taniguchi et al., 1979, Proc. Japan Acad. Ser. B 55, 461–469; Houghton et al., 1980, Nucleic Acids Res. 8, 2885–2894; Nagata et al., 1980, Nature, 284, 316–320; Nagata et al., 1980, Nature, 287, 401–408; Goeddel et al., 1981, Nature, 290, 20–26; Gray et al., 1982, Nature, 295, 503–508). IFNs-α and IFN-β have been purified to homogeneity and the partial protein sequences obtained confirm the derived IFN-β sequence and the sequences of some recombinant IFN-α's (Allen and Fantes, 1980, Nature, 287, 408–411; Knight et al., 1980, Science, 207, 525–526; Stein et al., 1980, Proc. Natl. Acad. Sci, USA, 77, 5716–5719; Zoon et al., Science, 207, 527–528). The cysteine at the 17 position of beta interferon has been replaced by serine (R. O'Connell, Genetic Technology News, 3: 2, July 1983, European patent Application No. 83306221.9).

Human IFN-α is specified by a multigene family comprising at least 14 different genes, with at least 3 additional pseudogenes and 4 other genes known to hybridize, but not yet sequenced (Weissman, 1982, 11th Annual UCLA Symposium on Molecular and Cellular Biology). In contrast, there is only one well characterised human IFN-β gene (Owerbach et al., 1981, Proc. Natl. Acad. Sci, USA, 78, 3123–3127). The IFN-γ gene differs from IFNs-α and -β by having three introns and thus displays another distinction between the Type I and Type II IFNs (Gray and Goeddel, 1982, Nature, 298, 859–863).

Homologies exist between members of the human IFN-α multigene family, and between human IFN-α and IFN-β genes. It appears that IFN-α and IFN-β genes are the products of an ancient gene duplication, and perhaps diverged early in vertebrate evolution (Taniguchi et al., 1980, Nature, 285, 547–549). In contrast, the IFN-α multigene family seems to have diverged much more recently, perhaps within the last 26 million years (Miyata & Hayashida, 1982, Nature, 295, 165–168).

While the mechanism of action of interferons is not completely understood, certain physiological or enzymatic activities respond to the presence of the interferons. These activities include RNA synthesis and protein synthesis. Among the enzymes induced by interferons is (2'-5')(A)$_n$ synthetase which is activated by double stranded RNA. This synthetase generates 2'-5' linked oligoadenylates from ATP which activates a latent endoribonuclease, RNAse L, which cleaves single stranded RNA such as messenger RNA (mRNA) and ribosomal RNA (rRNA). Interferon induces a protein kinase which phosphorylates at least one peptide chain initiation factor and inhibits protein synthesis (Lengyel, ibid p. 253).

Interferons have been shown to be negative growth regulators for cells by regulation of the (2'-5')A$_n$ synthetase activity (Creasey et al., Mol. and Cell Biol., 3, 780,786 1983). IFN-β was indirectly shown to be involved in the normal regulation of the cell cycle in the absence of inducers through the use of anti-IFN-β antibodies. Similarly, interferons have been shown to have a role in differentiation (Dolei et al., J. Gen. Virol 46: 227–236, 1980) and in immunomodulation (Gresser, Cell. Immunol. 34: 406–415, 1977).

Interferons may also alter methylation patterns of mRNAs and alter the proportion of fatty acids in membrane phospholipids, thereby changing the rigidity of cellular membranes. These and other mechanisms may respond to interferon-like molecules in varying degrees depending upon the structure of the interferon-like polypeptide. It is envisaged that an IFN-β with an IFN-α disulfide pattern may display a new advantageous phenotype. For example, IFNs which show a greater antiviral to antiproliferative activity (and viceversa) or have an enhanced activity/specificity against a particular virus infected tissue or transformed cell mass.

Increased stability is an expected result of the creation of new disulfide bonds. Stability is defined as increased resistance to denaturation, proteolytic enzymes and other physical or activity changes. The increase in stability results in improved recovery during production, increased storage life and prolonged activity in solution.

The design and synthesis of new interferon-like polypeptides composed of beta interferons with alpha interferon disulfide pattern may allow the selective activation of only part of normal interferon-induced activities. These hybrid polypeptides could then be used appropriately to activate the interferon systems. In addition, the affinity of these modified interferons for cell surface receptors may differ from that of naturally occuring interferons. This would allow selective or differential targeting of interferons for a particular cell type.

Novel interferons containing a modified cysteine pattern can be constructed for the cysteine pattern of alpha, beta or gamma interferons using the methods of this invention. That is, a human alpha interferon can incorporate the cysteine patterns of the human beta or human gamma interferons; a human beta interferon can incorporate the cysteine patterns of human alpha or human gamma interferons; and a human gamma interferon can incorporate the cysteine patterns of human alpha or beta interferons. Similarly, a combination cysteine pattern from two or more interferon classes can be substituted into the third interferon class.

BRIEF DESCRIPTION OF THE DRAWINGS

FIG. 1 is a summary flow chart illustrating the amino acid changes by site directed mutagenesis resulting in IFNX802, 803 and 804.

FIG. 2 illustrates the restriction map of Construction I.

FIG. 3 illustrates the restriction map of Constructions II through V.

FIG. 4 illustrates the site directed mutagenesis resulting in IFNX802.

FIG. 5 illustrates the site directed mutagenesis resulting in IFNX803.

FIG. 6 illustrates the site directed mutagenesis resulting in IFNX804.

FIG. 7 illustrates the restriction map of Constructions VI, VII and VIII.

DESCRIPTION OF THE MODIFIED INTERFERONS

Chart 1 illustrates the DNA sequence coding for the amino acid sequence of IFN802. In addition to the traditional three letter abbreviation for amino acids, at the bottom of the figure is the one letter abbreviations recommended by the IUPAC-IUB Commission on Biochemical Nomenclature: A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; and Y, tyrosine.

Chart 2 illustrates the DNA sequence coding for the amino acid sequence of IFNX803.

Chart 3 illustrates the DNA sequence coding for the amino acid of IFNX804.

Chart 4 illustrates the DNA sequence coding for the amino acid sequence of IFNX815.

Chart 5 illustrates the DNA sequence coding for the amino acid sequence of IFNX816.

Chart 6 illustrates the DNA sequence coding for the amino acid sequence of IFNX817.

Chart 7 illustrates the DNA sequence coding for the amino acid sequence of IFNX818.

Chart 8 illustrates the DNA sequence coding for the amino acid sequence of IFNX457.

SUMMARY OF THE INVENTION

One object of this invention is the reorganization of the position and number of cysteines in HuIFN-$\beta$ to a pattern analogous to that found in the HuIFN-$\alpha$ family, by the process of site directed mutagenesis of individual nucleotides of the HuIFN-$\beta$ coding sequence, so as to cause defined changes in the amino acid sequence of the HuIFN-$\beta$. The resultant modified HuIFN-$\beta$ molecules show different or novel properties from that of HuIFN-$\beta$, and may show properties similar to those exhibited by the HuIFN-$\alpha$ family. A summary flow chart of the construction of the modified HuIFN-62 IFNX802, 803, and 804 molecules are shown in FIG. 1. Similarly, the disulfide pattern and amino acid sequence of the alpha, beta and gamma human interferons can be combined to form new hybrid or modified interferons. Another object of the invention is to create disulfide linkages that improve the physical and pharmacological properties of modified interferons, including stability.

An object of the invention is the production of DNA sequences coding for the production of the modified-interferons IFNX 802, 803, 804, 815, 816, 817, 818 and 457 and the amino acid sequences themselves.

Another object of the invention is the production of a pharmaceutical composition containing a therapeutically effective amount of the modified-interferons which are useful for anti-viral, anti-proliferative, anti-tumor, immunomodulatory or immunogenic treatment. Yet another object of the invention is a method of producing the modified-interferons of the present invention utilizing microorganisms.

DESCRIPTION OF THE PREFERRED EMBODIMENTS

I. Rationale for construction

The coding sequences of the leukocyte (alpha) interferon (IFN-$\alpha$) family are distantly related to the sequence of the fibroblast (beta) interferon (IFN-$\beta$) gene, for example the coding sequence of HuIFN-$\alpha_1$ (D) is 45% homologous at the nucleotide level and 29% homologous at the amino acid level to HuIFN-$\beta$ (Taniguchi et al, Nature 285 547 (1980).

Secondary and tertiary structures of $\alpha$- and $\beta$-interferons have been derived by various computer modelling procedures. Sternberg and Cohen (Int.J.Biol.Macromol. 4 137 (1982)) have produced a model for interferon tertiary structure applicable either to alpha or beta interferon, suggesting that the in vivo structures of each type of interferon are similar.

Human interferon alpha's have been shown to contain four cysteines at positions 1, 29, 98, 138 (positions relate to the IFN-$\alpha_2$ (A) sequence) which have been shown to form two intramolecular disulfide bridges with bonds between cys 1 and cys 98, between cys 29 and cys 138 (Wetzel, Nature 289 606 (1981). Human interferon beta contains three cysteines, at positions 17, 31 and 141. Positions 31 and 141 in beta have been considered analogous to positions 29 and 138 in the interferon alpha family. It has been shown that alteration of $cys^{141}$ to $tyr^{141}$ abolishes interferon beta antiviral activity. Further it has been described that pre-treatment of HuIFN-$\beta$ with the reducing agent dithiothreitol abolishes antiviral activity (Shepard et al. Nature 294 563 (1981)). These observations have been taken to show that a disulfide bridge between cys 31—141 is essential for the activity of HuIFN-$\beta$.

The cysteine substitutions in the modified interferons may be in the analogous position of another interferon or in the same sequential amino acid position. From the same sequential position, the cysteine may be moved 1 to 4 amino acid positions toward either end of the polypeptide replacing the amino acid normally in that position. Therefore, the cysteine substituted for the third amino acid of human beta interferon may be alternatively substituted at amino acid positions 1, 2, 4, 5, 6, or 7. Similarly, the cysteine substitution at position 101 may also be at positions 97, 98, 99, 100, 102, 103, 104, or 105. These alternative position substitutions result in an altered stress level on the disulfide bond formed.

II. Outline of the technique of site directed mutagenesis

Site directed mutagenesis, using oligonucleotides to produce defined sequence alterations is perhaps the most specific means of producing mutants in vitro.

The background to the method involved is reviewed in Zoller and Smith (Nucleic Acids Res. 11(20) 6487 (1982)), which also details many of the technical aspects of the methodology.

To summarise the procedure, the desired nucleotide change(s) are identified and an oligonucleotide constructed which is complementary to the region 5' and 3' to the nucleotide of interest. At this position the nucleotide used is that which will be complementary to the desired mutation (e.g., FIGS. 4-6). Thus when the oligonucleotide is annealed to the coding sequence a mismatch occurs at the point of interest.

In order to produce the coding strand in a single stranded form the most practical means is to introduce the sequence into a bacteriophage which has both double stranded and single stranded DNA phases during its life cycle. Two phages commonly used are $\phi \times 174$ and M13. The bacteriophage M13 was used in this method.

After annealing of the oligonucleotide to the sequence to be mutated, closed circular molecules are transcribed and ligated. The complete molecules may be separated from incomplete transcripts either by separation on alkaline sucrose gradients (Zoller and Smith, 1982) or by electrophoresis and elution from low gelling temperature agarose. The latter technique has the advantage that subsequent transformation of the DNA into competent E.coli JM101 cells can be done in the presence of the agarose, as will be described, so reducing the number of manipulations.

Prior to separation of transcripts, by whichever means, incomplete transcripts may be degraded by $S_1$ nuclease to allow greater resolution during the separation stage. After transformation a population of mutant and wild type molecules are obtained which may be distinguished by one of a number of screening techniques.

For example, the desired change may introduce or delete a restriction endonuclease site which can be easily detected. Alternatively, the difference in $T_m$ (point of 50% irreversible melting) of hybrids formed between the oligonucleotide primer and either the original sequence of the mutant sequence can form the basis of a hybridization screening procedure (e.g., Zoller and Smith, 1982).

In order to increase the yield of mutants, the pool of transformed cells can be used to prepare a mixed population of single stranded (ss) DNA molecules. These can then be used as a template for a further round of annealing/transcription under conditions favouring the annealing of the oligonucleotide to the mutant sequence rather than the original sequence.

The DNA sequences illustrated in Charts 1 to 8 illustrate one preferred example of a DNA sequence that will code for the synthesis of the modified interferon amino acid sequence illustrated on the same chart. The genetic code (Lehninger, Biochemistry, Worth Publishing p. 962) will allow the design and synthesis (Nucleic Acids Research 11 477, 1983) of additional DNA sequences which also code for the amino acid sequences described in Charts 1 to 8. Such additional sequences could also be utilized in the plasmids pJA1, pJA2 and pJA3 to produce the modified-interferons of the present invention.

1. Constructions

TABLE 1

| NOMENCLATURE FOR CONSTRUCTIONS | | |
|---|---|---|
| CONSTRUCTION | TRIVIAL NAME | PRODUCT IDENTIFICATION |
| I | M13-1RB-00 | HuIFN-$\beta$ |
| II | M13-4AB-00 | HuIFN-$\beta$ |
| III | mJA1 | HuIFN-X802 |
| IV | mJA2 | HuIFN-X803 |
| V | mJA3 | HuIFN-X804 |
| VI | pJA1 | HuIFN-X802 |
| VII | pJA2 | HuIFN-X803 |
| VIII | pJA3 | HuIFN-X804 |

M13 is a bacteriophage, a bacterial virus, more particularly, a so-called "filamentous phage", which infects male Escherichia coli (E.coli) cells. Unlike many bacteriophages, the DNA found in the virus or phage particle is single stranded (ss DNA). Upon infection of an E.coli cell, the ss DNA is converted to the corresponding double stranded form (ds DNA) and amplified, under suitable conditions of growth, to, for example, from 200 to 300 copies per cell. The phage-infected cells do not lyse releasing the new phage particles, but continue to grow and divide, although at a reduced rate. This may be seen on agar plates as a lighter area, a "plaque", of slower-growing cells against a background of uninfected cells.

The ds DNA is also termed the "replicative form" (RF). This is comparable to a bacterial plasmid and may be used as a cloning and expression vector. The RF is central to the phage multiplication process. It is the template for ss DNA synthesis and for expression via protein biosynthesis of M13 phage genetic information. The former process produces phage particles and the latter allows the synthesis of phage proteins which are required to direct infected cells to produce further phage particles.

Wild type M13 has previously been modified for use as a cloning vehicle by the insertion of a fragment of E.coli DNA containing the lactose operon control region (lac promoter) and coding information for an active $\beta$-galactosidase ($\beta$-gal) in a non-essential region of the phage DNA. When the lac promoter is active, the expression of β-gal occurs and this is detected by a simple blue colour reaction in the infected cells. However, the cloning of DNA fragments generally results in the interruption of the lac Z gene and hence in colourless plaques due to the failure of β-gal expression. Thus, recombinants may be detected visually.

For example, U.K. Patent No. 1,588,572, which is directed to the production of filamentous hybrid phages, is representative of the stage of the art outlined above.

The known system allows the cloning of different-sized fragments of foreign DNA and the identification of recombinant clones without relying on the use of antibiotic resistance genes. Also, it allows the possibility of easily purifying phage ss DNA for use in recombinant characterisation and DNA sequencing, and site directed mutagenesis.

The known bacteriophage M13 mp 701 may be regarded as a starting point for the present invention. This vector, which is freely available, was constructed from M13mp7, which is commercially available, by known methods. Similarly, M13mp7 was in turn constructed from M13mp2. Reference may be made in this connection to, for example, Messing, J., et al, Proc.Natl.Acad.Sci.U.S.A., 74, 3642. (1977).

The plasmids pJA1, pJA2 and pJA3 in E coli K12 strain HB101 have the following ATCC designations; 39520, 39521 and 39522.

The American Type Culture Collection (ATCC) is located at 12301 Parklawn Drive, Rockville, Md. 20852 USA.

EXAMPLE 1

Construction I (M13-1RB-00, HuIFN-β)

Figure 2:
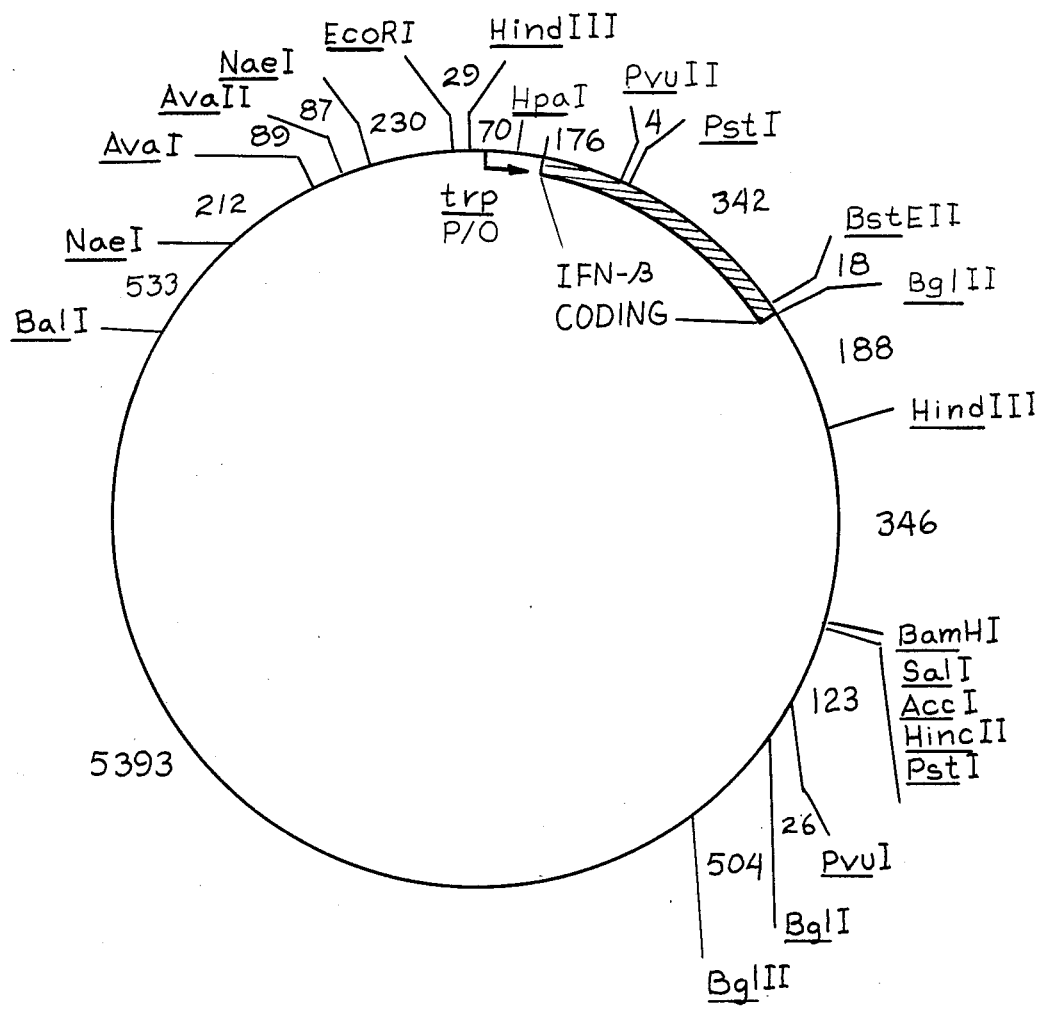

Recloning of a human fibroblast interferon gene plus trp promoter to give M13-1RB-00 (see FIG. 2):

A 1172 bp DNA fragment containing the trp promoter followed by the mature HuIFN-$\beta_1$ gene bounded on the left by an EcoRI site and on the right by a Bam HI site (GB patent application No. 2,068,970) was recloned between the EcoRI and Bam HI sites of phage M13 mp 701 as follows:

The joining of the EcoRI-Bam HI fragment containing the HuIFN-$\beta_1$ gene to the EcoRI-Bam HI digested M13 mp 701 vector was performed in an incubation of 50 ul containing: 0.25 μg vector; 0.9 μg EcoRI-Bam HI cut p1/24 (GB P). Approximately 8% of plaques on each plate were colourless, indicating the presence of recombinant phages (1RB-00). Recombinants were firmly identified by size and by nucleotide sequence analysis, also by expression of antiviral activity.

To prepare sufficient ss DNA for nucleotide sequence analysis, colourless plaques were picked and added to 2.5 ml YT medium containing 25 μl of a dense, overnight culture of E.coli K12 JM101. Phage was grown by aeration for 5 hours at 37° C. and the ss DNA purified by known methods, (see, for example, Sanger, F., et al, (J. Mol. Biol., 143, 161, 1980). The ss DNA was used as the template for dideoxy sequencing, (see, for example, Sanger, F., et al, Proc. Natl. Acad. Sci. U.S.A., 74, 5463, 1977). For example, the presence and sequence of the trp promoter and the presence of the HuIFN-β1 gene was established with an oligonucleotide primer, IFIA (GB patent application No. 2,068,970) which is known to prime in the HuIFN-β coding region.

EXAMPLE 2

Construction II (M13-4AB-00, HuIFN-β)

Figure 3:
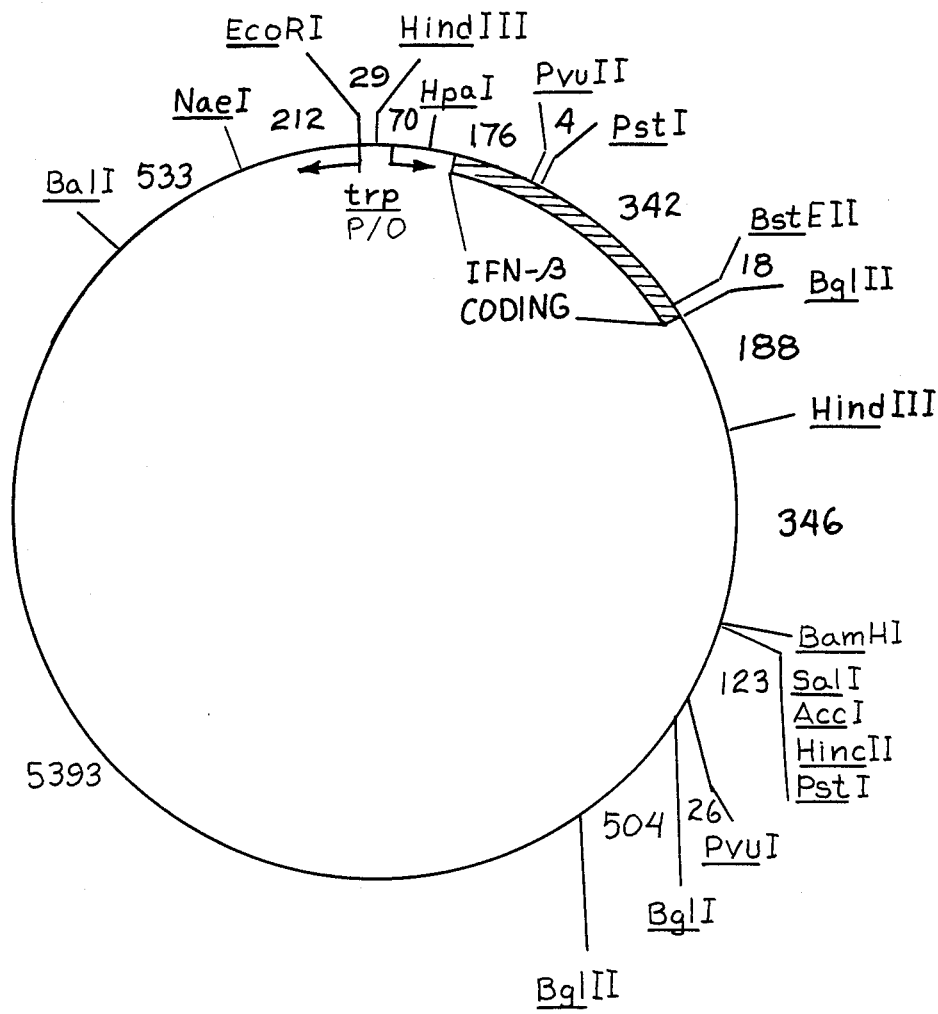

Deletion of the lac promoter from M13-1RB-00(I) to give a recombinant capable of expressing mature HuIFN-β under the control of only the trp promoter, II=M13-4AB-00) (See FIG. 3).

Construction of this clone was achieved by excision of a 406 bp Ava I-EcoRI fragment as follows: Ava I-EcoRI double digestion was effected in 100 μl containing: 10 μg ds DNA prepared from construction I, (see, for example, Birnboim, H.C., and Doly, J., Nucl. Acids Res., 7, 1513, 1979), 6 mM Tris-HCl, pH 7.5, 10 mM MgCl$_2$, 6 mM 2-mercaptoethanol, 30 mM NaCl, 15 units Ava I and 15 units EcoRI for 90 minutes at 37° C. The DNA was precipitated by the addition of 20 μg tRNA; 0.3 M NaAc, pH 4.5 to 0.3 M final concentration and 0.3 ml ethanol for 10 minutes at −70° C. Repair of protruding 5'-ends, with DNA polymerase, was then done in a 50 μl final volume.

To "fill-in" protruding 5'-ends, the DNA fragments were repaired in vitro with DNA polymerase I (Klenow fragment) in a 50 μl reaction containing 1 μg DNA in 10 mM NaCl, 50 mM Tris-HCl, pH 7.8, 10 mM MgCl$_2$, 1 mM 2-mercaptoethanol, 0 2 mM each deoxynucleoside 5'-triphosphate, 20 μg/ml. bovine serum albumin, 0.2 mM each deoxynucleoside 5'-triphosphate, and 1 unit of Klenow enzyme for 20 minutes at 14° C. in a volume of 50 μl, then for 10 minutes at 65° C.

The repaired DNA was self-ligated in a 50 μl incubation containing 5 μl of the above incubation (equivalent to 0.1 μg DNA), 66 mM Tris-HCl, pH 7.5, 5 mM MgCl$_2$, 20 mM DTT, 1 mM ATP, and 4.5 units T4 DNA ligase for 17 hours at 25° C. Uptake of DNA into CaCl$_2$-treated E.coli K12 JM101 and plating out of cells for plaques was performed using standard methods.

The identity of the new clone (M13-4AB-00) was confirmed by Tag I restriction analysis.

EXAMPLE 3

Construction III (mJA1), HuIFN-X802)

Alteration of Human Interferonβ (HuIFNβ) amino acid 3 (tyrosine) to cysteine, to give mJA1. (See FIGS. 3 and 4 and Chart 1).

A tetradecamer of the sequence 5' OH-AGT TGC AGC TCA TG-OH (FIG. 4) was constructed using standard phosphotriester chemistry; Reference: Nucleic Acids Research 11 477 (1983). This sequence is complementary to the sequence 5'C ATG AGC TAC AAC T which consists of the nucleotide preceding the initiator ATG followed by the first 13 nucleotides of the coding sequence of Human IFN-β- (GB patent application No. 2,068,970) with the exception that the 6th nucleotide of the primer, numbered from the 5' end corresponds to the complement of the desired mutation. This mutation will change the nucleotide A at position 8 of the coding sequence to a G.

Specific priming of the synthetic oligonucleotide to the region which was to be mutated was observed by the following procedure. First the oligonucleotide was labelled with [$^{32}$P] at the 5' terminus. 10 pmole of oligonucleotide was incubated in a total volume of 50 μl consisting of 50 mM Tris-HCl pH 7,6, 10 mM MgCl$_2$, 0.1 mM EDTA (ethylene diamine tetra acetic acid), 10 mM dithiothreitol, 0.1 Mm spermidine, 50 μCi [γ-$^{32}$P] ATP (5000 Ci/mmole, Amersham) and 5 units of polynucleotide kinase. The reaction mix was incubated at 37° C. for 60 minutes, followed by 65° C. for 5 minutes. The oligonucleotide was separated from unincorporated [$\gamma$-$^{32}$P] ATP by differential elution from a column of Whatman DE52 ion exchange resin (0.3 ml bed volume). The oligonucleotide was eluted in 0.5 M NaCl, 10 mM Tris HCl pH 7.5, 1 mM EDTA, 20 µg E.coli tRNA was added and the oligonucleotide was precipitated at −70° C. after the addition of three columes of ethanol. The oligonucleotide was redissolved in 8 µl of 10 mM Tris HCl pH 7.5, 1 mM EDTA.

5 pmoles of [$^{32}$P] oligonucleotide were annealed to 0.5 pmole of M13-4AB-00 in a total volume of 5 µl of 10 mM NaCl, 40 mM Tris-HCl pH 7.5, 20 mM MgCl$_2$, 2 mM 2-mercaptoethanol, by heating at 80° C. for 5 minutes followed by incubation at 20° C. for 1 hour.

The samples were adjusted to 67.5 mM NaCl, 45 mM Tris-HCL pH 7.5, 25 mM MgCl$_2$, 1 mM 2-mercaptoethanol, 83 uM each of dATP, dCTP, dGTP, dTTP and 0.5 unit of the 'Klenow' fragment of DNA Polymerase I (BRL Inc.) in a final volume of 15 µl. The samples were incubated at 25° C. for 4 hours. The samples were diluted eight fold with 10 mM Tris-HCL pH 7.5, 1 mM EDTA, heated to 65° C. for 5 minutes, adjusted to 0.3 M Na acetate pH 4.6 and finally the nucleic acid was precipitated with three volumes of ethanol at −70° C. for 15 minutes. In order to identify specific priming products the samples were digested with the enzyme EcoRl and the products separated by electrophoresis through a 7 M Urea, 6% Acrylamide, 0.3% Bis (NN′-methylene bisacrylamide) gel prepared in 135 mM Tris-HCL pH 8.8, 45 mM Na borate, 1 mM EDTA.

A specific transcription product of 150 bases was identified which corresponds to the instance between the upstream E.coli site in 4AB-00 and the 5′ end of the oligonucleotide, given specific priming.

Formation of complete closed circular molecules was achieved as follows: The oligonucleotide was phosphorylated as described earlier except that ATP at 1 mM final concentration replaced the [$\gamma$-$^{32}$P] ATP. The oligonucleotide was annealed as described earlier except that a primer to template ratio of 100 was used (50 pmole oligonucleotide per 0.5 pmole template).

The transcription and ligation of the product was performed as follows: 10 µl of anealed primer-template, containing 0.5 pmole of template and 50 pmole of primer in 100 mM NaCl, 40 mM tris-HCl pH 7.5, 20 mM MgCl$_2$, 2 mM 2-mercaptoethanol was adjusted to a volume of 20 µl containing 20 µCi [$\alpha^{32}$P] d ATP (2000ci/mmole) 250 µMm each of dATP, dCTP, dGTP, dTTP, 0.8 unit of Klenow DNA polymerase I, 2 units T$_4$ ligase (BRL Inc.) in 67.5 mM NaCl, 45 mM Tris pH 7.5, 25 mM MgCl$_2$, 1 mM 2-mercaptoethanol. After 30 minutes at 22° C. dATP was added to 250 µM and a further 0.8 unit of Klenow DNA polymerase was added. The mixture was incubated a further 2.5 hours at 22° C. The DNA was adjusted to 0.3 M Na acetate pH 4.6, and precipitated with three volumes of ethanol at −20° C. overnight (16 hrs).

Incomplete transcripts were digested with S1 nuclease as follows. The DNA was incubated for 30 minutes at 25° C. in a solution of 300 mM NaCl, 5 mM ZnCl$_2$, 30 mM Na acetate pH 4.5 at an initial template concentration of 1 nM in a final volume of 250 µl. S1 nuclease was added at the rate of 1 unit per 0.01 pmole of initial template.

The products were added directly to 0.4 mls of competent E.coli JM101 at 0° C. After 40 minutes the cells were heat shocked for 2 minutes at 42° C. then diluted into 20 ml of YT broth (8 g tryptone, 5 g yeast extract, 5 g NaCl per liter) at 37° C. The cells were grown at 37° C. for 16 hours. The cells were pelleted by centrifugation and phage in the supernatent were stored in 60% glycerol at −20° C.

Dilutions of phage were plated on indicator cells and plates containing 2–400 plaques were used to make nitrocellulose replicates for hybridization, using the [$^{32}$P] phosphorylated oligonucleotide as probe in a manner similar to that of Benton and Davis (Science 196, 180, 1977). Filters were prewashed in 6×SSC at 40° C. for 3 hrs and hybridized using 300 µl of a solution of 6×SSC/10×Denhardts/0.1% SDS containing primer at 400 pM for 16 hrs at 40° C., under paraffin oil [1×SSC=0.15 M. NaCl; 0.015 M Na citrate, pH 7.2. 10×Denhardts=0.2% Bovine Serum Albumin (BSA); 0.2% polyvinyl pyrollidone (PVP); 0.2% Ficoll]. Filters were washed in 6×SSC/0.1% SDS at 15° C., with six changes of five minutes each.

Fifty plaques which showed hybridization above background were picked into 50 µl each of LTB (10 mM Tris-HCl pH 7.5, 20 mM NaCl, 1 mM EDTA). Cellular debris was spun out and 1 µl of supernatant for each plaque was spotted onto a lawn of E.coli JM101 which had been allowed to grow for 60 minutes at 37° C. After overnight growth large plaques were formed on the lawn of E.coli JM101. Nitrocellulose replicates were again taken and hybridised as above. Nineteen of the 50 plaques showed hybridization above control levels. These were rescreened exactly as described above. Six were taken for further analysis by DNA sequencing. As the desired change was A to G, the coding strand was analysed by 5′end-labelling followed by the G reactions of the Maxam and Gilbert chemical degradation sequencing technique (Maxam and Gilbert, Methods in Enzymology Vol 65 (1), p 499, 1980) while the non-coding strand was analysed by 3′ end-labelling followed by the 'C' reaction of the Maxam and Gilbert technique. Thus mutants would exhibit an extra G in the coding strand and an extra C in the non-coding strand compared to parallel reactions on the parent M13-4AB-00. The DNAs were therefore digested with either Hind III to produce staggered ends for 3′ labelling, or Hpa I to produce a blunt end for 5′ labelling.

After labelling the fragments were digested with Bgl II to separate the labelled ends. The required fragments were isolated by electrophoresis on a 10% Acrylamide/0.33% bis-acrylamide gel in 135mM Tris-HCl pH 8.8, 45 mM Na borate, 1 mM EDTA. The fragments were electroeluted and concentrated on a 0.3 ml Whatman DE52 ion exchange resin column prior to DNA sequencing. All six clones showed the desired change. Two of the clones were picked and tested to show that the gene product was still antivirally active.

Interferon anti-viral assays were performed on extracts of M13 infected or plasmid transformed cells as follows: Fifty 200 ml. cultures in tryptophan-free minimal medium plus glucose were harvested at an optical density (600 nm) of 0.6–0 g by centrifugation at 10,000 rpm for 10 minutes. The cells were then frozen at −70° C., thawed in the presence of 2.5–5.0 ml of 15% (w/v) sucrose; 50 mM Tris-HCl, pH 8.0; 0.1% (w/v) human serum albumin and 2.5 mg lysozyme, then incubated at 20° C. for 15 minutes with shaking. The cell debris was removed by centrifugation at 15,000 rpm for 20 minutes and the supernatant was further clarified and sterilised by filtration through a 0.22 um pore diameter nitrocellulose filter. Finally the extract was assayed for anti-viral activity by monitoring the protection conferred on Vero (African green monkey) cells against the cpe (cytopathic effect) of EMC (Encephalomyocarditis) virus infection in an in vitro microplate assay system (see, for example, Dahl, H., and Degre, M., Acta. Path. Microbiol. Scan., 1380, 863 1972).

Similar levels of antiviral activity to that shown by the parent were observed. Single-stranded phage DNA was isolated from one clone by established procedures, to act as template for construction IV.

EXAMPLE 4

Construction IV (mJA2, HuIFN-X803)

Alteration of mutant interferon $\beta$ (mJA1) at amino acid 101 (valine) to cysteine, to give mJA2. (See FIGS. 3 and 5 and Chart 2).

An octadecamer of sequence 5' OH-CTTCCAGG-CATGTCTTCA-OH 3' (FIG. 5) was constructed using phosphotriester chemistry, as for Construction III. This sequence is complementary to the sequence 5'TGAAGACAGTCCTGGAAG.3' which comprises nucleotides 294 to 310 of the IFN-$\beta_1$ coding sequence (see published GB patent application No. 2,068,970) with the exception that the 9th and 10th nucleotides of the oligonucleotide, numbered from the 5' end, correspond to the complement of the desired mutations. Thus the desired changes will be from G at nucleotide 301 of the coding sequence to T, and from T at nucleotide 302 to G.

Specific priming was demonstrated exactly as for mJA1. The specific product was identified as a 348 base fragment after digestion of the transcription products with Hpa I and electrophoresis as previously described.

Formation of closed circular molecules, ligation, transfection were as described from Example 3. Phage DNA was prepared from the total pool of transformants and used as a template for reannealing of the primer, transcription, ligation, S$_1$ nuclease treatment, and transfection as described, except that in the S$_1$ reaction the conditions were changed to encourage digestion at the mismatch between parent template and primer, so enriching for mutant closed circular molecules in the population. The reaction therefore was performed in 300 $\mu$l of 100 mM NaCl, 30 mM Na acetate Ph 4.5, 5 mM Zncl and containing 0.8 pmole of initial template and 2 units of S$_1$ nuclease.

Phage DNA was prepared from the total pool of transformants and the enrichment stage was repeated again exactly as above. 50 plaques from the second round of enrichment were grown in 1 ml (YT medium). 2 $\mu$l of each suspension was spotted directly onto nitrocellulose and hybridised as above. Three positive plaques and two negative plaques were rescreened. Phage DNA was prepared and concentrated by polyethylene glycol (PEG) precipitation. Phage were resuspended in 50 $\mu$l of LTB, representing a 300 fold concentration. 2 $\mu$l of each suspension was spotted onto nitrocellulose and hybridised with [$^{32}$P] phosphorylated primer as described above. Hybridization confirmed the three positive plaques. The presence of the desired change was confirmed by DNA sequencing (Maxam and Gilbert). Single stranded phage DNA was prepared by established procedures. A short oligomer complementary to the sequence coding for amino acids 114 to 117 of the $\beta$ sequence was prepared and phosphorylated using [$\gamma$-$^{32}$P] ATP as described previously. This was annealed to the phage DNA as described and short transcripts produced which were cleaved with Pst 1. A band of 213 b. corresponding to the specific priming product was isolated on a 7M urea, 8% Acrylamide 0.2% Bis-acrylamide 135 mM Tris-HCl pH 8.8, 45 mM Na borate, 1 mM EDTA gel. The fragment was electroeluted and the DNA sequenced using the Maxam and Gilbert technique. The DNA sequence confirmed the desired changes (FIGS. 5, 6). One clone was picked and tested to show that the gene product was still antivirally active as described earlier. This clone was used as a template for construction V.

EXAMPLE 5

Construction V (mJA3, HuIFN-X804)

Alteration of mutant human interferon $\beta$ (mJA2) at amino acid 17 (cysteine) to serine to give mJA3 (See FIGS. 3 and 6 and Chart 3).

A hexadecamer of sequence 5'OH-CTGACTCT-GAAAATTG3' (See FIG. 6) was constructed using phosphotriester chemistry, as for Construction III and IV. This sequence is complementary to the sequence 5'CAATTTTCAGTGTCAG3' which comprises nuclotides 39 to 54 inclusive of the IFN-$\beta$ conding sequence (see published GB patent application No. 2,068,970) with the exception that the 6th nucleotide of the oligonucleotide, numbered from the 5' end,, corresponds to the complement of the desired mutation. Thus the desired change will be from T to A at nucleotide 49 of the coding sequence.

Specific priming was demonstrated as for Example 3 and 4. The specific product was identified as a 187 base fragment after digestion of the transcription products with EcoRI and electrophoresis as previously described.

Formation of closed circular molecules and ligation was as described for constructions III and IV. Closed circular molecules were separated from incomplete products by electrophoresis through 1% low melting temperature agarose in 67.5 mM Tris-HCl pH8.8, 22.5 mM Na borate, 0.5 mM EDTA, 1 $\mu$g/ml ethidium bromide without prior S$_1$ nuclease treatment. The region corresponding to closed circular double stranded full length molecules was visualised under long wave (366 nm) transillumination, cut from the gel and melted at 60° C. for 5 minutes. A volume corresponding to 0.3 pmole of double stranded product was used to transfect E.coli JM101 by established procedures. The transfected cells were plated out in top agar directly. After overnight growth, nitrocellulose replicates were taken and hybridized with [$^{32}$P] phosphorylated primer as described. The hybridization temperature was 42° C. for 36 hours. E.coli DNA (10 $\mu$g/ml, heat denatured) was included in the prehybridization solution. Finally, the filters were washed at 44° C. in 6 x SSC.

The 24 plaques which showed a signal above background were picked and grown for 6 hours in 1 ml YT broth containing 25 $\mu$of log phase E.coli JM101. The cells were removed by centrifugation and the phage in solution were concentrated 80 fold by PEG precipitation, to a final volume of 10 $\mu$l. 4 $\mu$l of each was spotted onto nitrocellulose and hybridized using the [$^{32}$P] primer. About 50% of the spots showed a signal greater than the background level. Four of the positive phage were further plaque purified. Phage was isolated from distinct, positively hybridizing plaques and the dsDNA replicative form (RF) prepared. The presence of the desired change was inferred by the appearance of a novel Hinf 1 site. The desired change, T to A, introduces the sequence 5' GAGTC which is a recognition sequence from the enzyme Hinf I. The presence of the site causes a Hinf I fragment of 197 base pairs in the parent RF to be cleaved to two molecules of 169 and 28 base pairs in the mutant RF.

Thus 5 μg of RF was digested with 12.5 units of Hinf I in a total volume of 500 ul of 6 mM Tris-HCl pH 7.5, 6 mM MgCl$_2$, 6 mM 2-mercaptoethanol, 50 mM NaCl. for 16 hours at 37° C. The fragments were labelled at their 3' ends with [$^{32}\alpha$P] dATP as the restriction enzyme cleaves between the G and A of the recognition site. Thus the reaction consisted of 0.4 pmole of DNA, 20 μCi [α-$^{32}$P] dATP (2000Ci/mmole) and 2 units of Klenow DNA polymerase I in 50 μl of 6 mM Tris-HCl pH 7.5, 50 mM NaCl, 6 mM MgCl$_2$, 7 mM mercaptoethanol, at 25° C. for 60 minutes. The fragments were separated on 10% acylamide, 0.33% Bis-acrylamide, in 135 mM Tris-HCl pH 8.8, 45 mM Na borate, 1 mM EDTA. All of four plaques analysed showed the desired restriction pattern indicating the desired mutation had been induced.

EXAMPLE 6

Constructions VI, VII, VIII

VI: pJA1, HuIFN-X802
VII: pJA2, HuIFN-X803
VIII: pJA3, HuIFN-X8041

Subcloning of mutant β constructs into pMN39-1. (See FIG. 7).

Plasmid pMN39-1 consists of a deletion of 434 bp between the Bgl 11 and Bam HI site of plasmid pl-24. pMN39-1 therefore contains the natural HuIFN-β gene under trp attenuator minus control. The trp control region and 161 amino acids of the IFN-β, gene are present on a 621 bp EcoRI/BstEII fragment. This fragment can be removed and replaced by the analogous fragments from mJA1, mJA2 or mJA3 to produce pJA1, pJA2, pJA3 respectively. These constructs would thus represent the mutant HuIFN-β genes under trp control on a high copy number plasmid also coding for the β-lactamase gene so allowing selection by conferring ampicillin resistance on a transformed E.coli cell.

In order to achieve the subcloning RF from mJA1, mJA2, mJA3, and closed circular plasmid pMN39-1 were digested with the enzymes EcoRI and BstEII. One pmole each of mJA1, mJA2 and mJA3 were digested with 10 units of BstEII for 16 hours at 37° C. in a total volume for each reaction of 250 μl. 2 pmole of pMN39-1 was digested with 10 units of BstEII for 16 hours at 37° C. in a total volume of 250 μl.

The DNAs were precipitated and redigested with 20 units each of EcoRI for 16 hours at 37° C. in a total volume of 250 μl. The digestion products were precipitated and redissolved in 20 μl of 10 mM Tris-HCl pH 7.5, 1 mM EDTA. The products of the digestion of pMN39-1 were resolved on a 0.8% low melting temperature agarose gel in 67.5 mM Tris-HCl pH 8.8, 22.5 mM Na borate, 0.5 mM EDTA containing 1 μg/ml ethidium bromide. The 3303 bp EcoRl/BstEII fragment was cut from the gel and melted at 60° C.

The products of the digestion of mJA1, mJA2, mJA3 were resolved as above except that the agarose concentration was 2%. The 621 bp EcoRI/BstEII fragment from each digest was cut from the gel and melted at 60° C.

A volume calculated to contain 0.17 pmole of the 3.3 kb pMN 39-1 fragment was mixed with a volume calculated to contain 0.4 pmole of the 0.62 kb fragment for each of mJA1, mJA2, mJA3. The fragments were ligated with 1 unit of T4 ligase in a total volume of 200 μl of 65 mM Tris-HCl pH 7.5, 5 mM Mg Cl$_2$ 20 mM dithiothreitol, 1 mM ATP for 24 hours at 20° C.

Fifty μl of each ligation mix was used to transform 0.3 ml of competent E.coli K12 HB101 cells by established procedures.

Several transformants for each ligation were grown and plasmid DNA prepared by the method of Birnboim and Doly (Nucleic Acids Res. 7 1573 1979). The plasmid DNA was digested with HinfI and compared against pMN39-1 as described for the analysis of Construction V. For pJA1 and pJA2 the digestion pattern was shown to be identical to pMN39-1. The HinfI digest of pJA3 differed from that of pMN39-1 in that the 197 bp band was not present but was replaced by bands of 169 and 28 bp, as expected.

EXAMPLE 7

Antiviral properties of modified IFN-β

Antiviral assays were performed as described in the description of the construction of mJA1 (Construction III).

In the cases of constructions VI - VIII the medium contained ampicillin at 100 ug/ml.

Yields of interferon were obtained for constructions I–IV as indicators that the constructs still retained biological activity (Table 2). The A600 was 0.4 when induced and 1.0 when harvested. In all cases expression from the trp promoter could be detected in inducing conditions. However, yields ranged from $6 \times 10^3$ to $5.3 \times 10^4$ Iu./L for mJA3 (Construction II), $3.7 \times 10^3$ to $7.9 \times 10^4$ IU/L for mJA1 (Construction III), and $1.45 \times 10^3$ to $2 \times 10^5$ IU/L for mJA2 (Construction IV).

TABLE 2

| Experiment No. | Construct | (Trivial Name) | Antiviral Titre IU/L | Mean IU/L |
|---|---|---|---|---|
| 1. | | pMN39-1 | $2.3 \times 10^7$ | $2.3 \times 10^7$ |
| | VI | pJA1 | $4.8 \times 10^5$ | $6.2 \times 10^5$ |
| | VI | pJA1 | $7.6 \times 10^5$ | |
| | VII | pJA2 | $1.14 \times 10^6$ | $1.2 \times 10^6$ |
| | VII | pJA2 | $1.33 \times 10^6$ | |
| 2. | | pMN39-1 | $3.5 \cdot 10^7$ | |
| | VII | pJA2 | $6.65 \times 10^6$ | |
| 3. | | pMN39-1 | $6.35 \times 10^6$ | |
| | VII | pJA2 | $3 \times 10^5$ | |
| | VIII | pJA3 | $2.1 \times 10^6$ | |

The antiviral titres of the plasmid constructs VI to VIII have been investigated. Experiments (Table 2) indicated a reduction in the titre compared to the parental plasmid pMN39-1. In particular the A to G alteration from pMN39-1 to pJA1 results in an apparent drop in the titre of more than one order of magnitude.

| SUMMARY OF TABLE 2 | |
|---|---|
| Construct (Trivial Name) | Antiviral Titre (IU/L) |
| pMN39-1 | $2.14 \times 10^7$ |
| pJA1 | $6.2 \times 10^5$ |
| pJA2 | $2.35 \times 10^6$ |
| pJA3 | $2.1 \times 10^6$ |

Data from heterologous cell assays performed with crude lysate material indicate no alteration in activity between the pMN39-1 product and that of pJA1 and pJA2.

Determination of —SH groups in proteins

The presence of sulfhydral groups S in the modified interferons is determined by spectrophotometric titration with p-mercuribenzoate by the method of Boyer (1954). Boyer P.D. (1954), J.Amer.Chem. Soc. 76,4331. This method is performed in, for example, 8M urea or 0.5 to 1% sodium dodecyl sulphate to "unmask" buried —SH groups. Other methods based on alkylation reactions are appropriate, e.g. use of N-ethylmaleimide (NEM). Gregory, J.D. (1955), J.Amer.Chem.Soc. 77,3922. One can also use methods based on reactions with disulphides e.g. 5,5'-dithiobis (2-nitrobenzoate) by the method of Ellman (1959). Arch.Biochem. and Biophys. 82, 70, yielding a chromophore which may be quantitated spectrophotometrically.

Determination of —S—S— groups in proteins

The methods used for determining the sulfhydral (—SH) content of proteins are applicable to the determination of the (—S—S—) disulfide (—S—S—) content, after first reducing the —S—S— bridges with a reducing agent. The number of —S—S— bonds may then be deduced from knowledge of the number of —SH groups in the non-reduced protein relative to the total —SH content after reduction. For example, a method was developed by Cavallini et al (1966), Nature 212,294 where —S—S— groups were reduced with borohydride, and the number of —SH groups formed determined by using the method of Ellman (ibid).

Determination of the position of disulphide bonds in proteins

The formation of strongly acidic sulphonic groups by the oxidative cleavage of S—S bonds sharply changes the electrophoretic mobility of peptides containing cysteine. Brown and Hartley (1963,1966) (1963,Biochem.J., 89,59P) (1966,Biochem.J., 101,214) developed a method for locating S—S bridges in proteins using "diagonal electrophoresis" of peptides on paper. An enzymic hydrosylate is subjected to electrophoresis at pH6.5. After drying, a strip is cut out from the electrophore- gram and is sewn onto a new sheet of paper. A second electrophoresis is then carried out at pH6.5 at a right angle to the direction of the first electrophoresis. As a result, the peptides are arranged, according to their mobilities, along a diagonal line. If the strip of paper cut out after the first electrophoresis is exposed to vapours of performic acid, the peptides containing cysteic acid formed by this treatment are located off the diagonal. By this method, one easily identifies the peptides that are linked in a protein by S—S bridges.

Such peptides are eluted from the paper and subjected to amino-acid analysis and/or peptide sequencing and thus the location of peptide bonds in the protein determined.

EXAMPLE 8

Construction of IFNX815, IFNX816, IFNX817, IFNX818, and IFNX457

The DNA nucleotide sequence and amino acid sequence of the modified-interferons IFNX815, 816, 817, 818, and 457 are shown in charts 4–8. These DNA sequences are constructed from the plasmids pJA1, pJA2, and pJA3 utilizing the methods of Examples 3, 4, 5, and 6. The modified interferons are isolated using the methods of Example 9. Alternatively, an entire DNA sequence specified by charts 4–8 is synthesized using the standard genetic code indicating triplet codons and standard phosphotriester chemistry of Examples 3, 4, and 5. Plasmids pMN39-1, pJA1, pJA2, or pJA3 are then utilized to produce the plasmids utilizing the method of Example 6.

EXAMPLE 9

Interferon Extraction and Purification

The interferons can be isolated from the producing cell by use of the following procedure:
Step 1. Centrifugation of broken cell preparation.
Step 2. Resuspend the pellet in 50 mM Tris-Cl pH 8.0 with three-fold w/w/ excess of SDS over protein. Add DTT to 100 mM and warm to 95°. Hold at 95° for five minutes.
Step 3. Centrifuge to obtain a clarified extract.
Step 4. Gel filter on an AcA44 column (4.4 X 60 cm) with 50 mM Tris-Cl pH 8.0, 10 mM DTT, 0.5% SDS as eluent, 40 ml/hr. This column size will allow the proceeds of a nominal 10 L fermentation (at the current cell density) to be processed in one batch.

Parenteral Administration

The modified interferons of the present invention can be formulated according to methods well known for pharmaceutical compositions, wherein the active interferon polypeptide is combined in admixture with a pharmaceutically acceptable carrier vehicle, such as albumin. Remington's Pharmaceutical Sciences by E. W. Martin, hereby incorporated by reference, describes composition and formulations suitable for delivery of the interferons on the present invention.

Pharmaceutical compositions of the present invention will contain an effective amount of the interferon protein together with a suitable carrier allowing therapeutic administration. One mode of administration is parenteral, another mode of administration is nasal spray.

Administration of the interferon composition is indicated for patients requiring antitumor cell growth or immune modulation, or antiviral treatment. Dosage and dose rate may parallel those now in use in clinical trials of approximately $10^5$ to $10^8$ units daily. Dosages significantly below or above these levels may be indicated in long term administration or during acute short term treatment. It is anticipated that a preferred dosage rate is $10^6$–$10^7$ units daily for parenteral administration.

We claim:

1. A modified beta interferon comprising a beta interferon wherein the tyrosine located at position 3 of natural beta interferon is replaced with cysteine.

2. A modified beta interferon comprising a beta interferon wherein the tyrosine located at position 3 of natural beta interferon is replaced with cysteine and the valine located at position 101 of natural beta interferon is replaced with cysteine.

3. A modified beta interferon comprising a beta interferon wherein the tyrosine located at position 3 of natural beta interferon is replaced with cysteine, the cysteine located at position 17 of natural beta inerferon is replaced with serine, and the valine located at position 101 of natural beta interferon is replaced with cysteine.

4. A pharmaceutical composition for use in the treatment of viral infections in an animal comprising an effective therapeutic amount of the modified beta interferon of claim 1 admixed with a pharmaceutically acceptable carrier.

5. A pharmaceutical composition for use in the treatment of viral infections in an animal comprising an effective therapeutic amount of the modified beta interferon of claim 2 admixed with a pharmaceutically acceptable carrier.

6. A pharmaceutical composition for use in the treatment of viral infections in an animal comprising an effective therapeutic amount of the modified beta interferon of claim 3 admixed with a pharmaceutically acceptable carrier.

7. A method of treating viral infections in an animal in need of such treatment comprising the administration of an effective amount of a modified beta interferon of claim 1.

8. A method of treating viral infections in an animal in need of such treatment comprising the administration of an effective amount of a modified beta interferon of claim 2.

9. A method of treating viral infections in an animal in need of such treatment comprising the administration of an effective amount of a modified beta interferon of claim 3.

* * * * *

UNITED STATES PATENT AND TRADEMARK OFFICE
CERTIFICATE OF CORRECTION

PATENT NO. : 4,751,077

DATED : June 14, 1988

INVENTOR(S) : Bell, et al.

It is certified that error appears in the above-identified patent and that said Letters Patent is hereby corrected as shown below:

Charts 1-8, as described in column 3, lines 52-68, and column 4, lines 1-10, under the heading "DESCRIPTION OF THE MODIFIED INTERFERONS", are missing from the patent and should read as follows:

IFNX 882

IFNβ[Tyr$^3$ -> Cys$^3$]

```
          5                    10                   15
MET-SER-CYS-ASN-LEU-LEU-GLY-PHE-LEU-GLN-ARG-SER-SER-ASN-PHE-
ATG AGC TGC AAC TTG CTT GGA TTC CTA CAA AGA AGC AGC AAT TTT
         20                    25                   30
GLN-CYS-GLN-LYS-LEU-LEU-TRP-GLN-LEU-ASN-GLY-ARG-LEU-GLU-TYR-
CAG TGT CAG AAG CTC CTG TGG CAA TTG AAT GGG AGG CTT GAA TAC
         35                    40                   45
CYS-LEU-LYS-ASP-ARG-MET-ASN-PHE-ASP-ILE-PRO-GLU-GLU-ILE-LYS-
TGC CTC AAG GAC AGG ATG AAC TTT GAC ATC CCT GAG GAG ATT AAG
         50                    55                   60
GLN-LEU-GLN-GLN-PHE-GLN-LYS-GLU-ASP-ALA-ALA-LEU-THR-ILE-TYR-
CAG CTG CAG CAG TTC CAG AAG GAG GAC GCC GCA TTG ACC ATC TAT
         65                    70                   75
GLU-MET-LEU-GLN-ASN-ILE-PHE-ALA-ILE-PHE-ARG-GLN-ASP-SER-SER-
GAG ATG CTC CAG AAC ATC TTT GCT ATT TTC AGA CAA GAT TCA TCT
         80                    85                   90
SER-THR-GLY-TRP-ASN-GLU-THR-ILE-VAL-GLU-ASN-LEU-LEU-ALA-ASN-
AGC ACT GGC TGG AAT GAG ACT ATT GTT GAG AAC CTC CTG GCT AAT
         95                   100                  105
VAL-TYR-HIS-GLN-ILE-ASN-HIS-LEU-LYS-THR-VAL-LEU-GLU-GLU-LYS-
GTC TAT CAT CAG ATA AAC CAT CTG AAG ACA GTC CTG GAA GAA AAA
        110                   120                  125
LEU-GLU-LYS-GLU-ASP-PHE-THR-ARG-GLY-LYS-LEU-MET-SER-SER-LEU-
CTG GAG AAA GAA GAT TTC ACC AGG GGA AAA CTC ATG AGC AGT CTG
        130                   135                  140
HIS-LEU-LYS-ARG-TYR-TYR-GLY-ARG-ILE-LEU-HIS-TYR-LEU-LYS-ALA-
CAC CTG AAA AGA TAT TAT GGG AGG ATT CTG CAT TAC CTG AAG GCC
        145                   150                  155
LYS-GLU-TYR-SER-HIS-CYS-ALA-TRP-THR-ILE-VAL-ARG-VAL-GLU-ILE-
AAG GAG TAC AGT CAC TGT GCC TGG ACC ATA GTC AGA GTG GAA ATC
        160                   165                  170
LEU-ARG-ASN-PHE-TYR-PHE-ILE-ASN-ARG-LEU-THR-GLY-TYR-LEU-ARG-
CTA AGG AAC TTT TAC TTC ATT AAC AGA CTT ACA GGT TAC CTC CGA

ASN-TER-
AAC TGA
```

MSCNLLGFLQRSSNFQCQKLLWQLNGRLEYCLKDRMNFDIPEEIKQLQQFQKEDAALTIY
EMLQNIFAIFRQDSSSTGWNETIVENLLANVYHQINHLKTVLEEKLEKEDFTRGKLMSSL
HLKRYYGRILHYLKAKEYSHCAWTIVRVEILRNFYFINRLTGYLRN<

CHART 1

UNITED STATES PATENT AND TRADEMARK OFFICE
CERTIFICATE OF CORRECTION

PATENT NO. : 4,751,077

DATED : June 14, 1988

INVENTOR(S) : Bell, et al.

It is certified that error appears in the above-identified patent and that said Letters Patent is hereby corrected as shown below:

IFNX 803

IFN$\beta$(Tyr$^3$ -> Cys$^3$)(Val$^{101}$ -> Cys$^{101}$)

```
              5                   10                  15
MET-SER-CYS-ASN-LEU-LEU-GLY-PHE-LEU-GLN-ARG-SER-SER-ASN-PHE-
ATG AGC TGC AAC TTG CTT GGA TTC CTA CAA AGA AGC AGC AAT TTT
              20                  25                  30
GLN-CYS-GLN-LYS-LEU-LEU-TRP-GLN-LEU-ASN-GLY-ARG-LEU-GLU-TYR-
CAG TGT CAG AAG CTC CTG TGG CAA TTG AAT GGG AGG CTT GAA TAC
              35                  40                  45
CYS-LEU-LYS-ASP-ARG-MET-ASN-PHE-ASP-ILE-PRO-GLU-GLU-ILE-LYS-
TGC CTC AAG GAC AGG ATG AAC TTT GAC ATC CCT GAG GAG ATT AAG
              50                  55                  60
GLN-LEU-GLN-GLN-PHE-GLN-LYS-GLU-ASP-ALA-ALA-LEU-THR-ILE-TYR-
CAG CTG CAG CAG TTC CAG AAG GAG GAC GCC GCA TTG ACC ATC TAT
              65                  70                  75
GLU-MET-LEU-GLN-ASN-ILE-PHE-ALA-ILE-PHE-ARG-GLN-ASP-SER-SER-
GAG ATG CTC CAG AAC ATC TTT GCT ATT TTC AGA CAA GAT TCA TCT
              80                  85                  90
SER-THR-GLY-TRP-ASN-GLU-THR-ILE-VAL-GLU-ASN-LEU-LEU-ALA-ASN-
AGC ACT GGC TGG AAT GAG ACT ATT GTT GAG AAC CTC CTG GCT AAT
              95                  100                 105
VAL-TYR-HIS-GLN-ILE-ASN-HIS-LEU-LYS-THR-CYS-LEU-GLU-GLU-LYS-
GTC TAT CAT CAG ATA AAC CAT CTG AAG ACA TGC CTG GAA GAA AAA
              110                 120                 125
LEU-GLU-LYS-GLU-ASP-PHE-THR-ARG-GLY-LYS-LEU-MET-SER-SER-LEU-
CTG GAG AAA GAA GAT TTC ACC AGG GGA AAA CTC ATG AGC AGT CTG
              130                 135                 140
HIS-LEU-LYS-ARG-TYR-TYR-GLY-ARG-ILE-LEU-HIS-TYR-LEU-LYS-ALA-
CAC CTG AAA AGA TAT TAT GGG AGG ATT CTG CAT TAC CTG AAG GCC
              145                 150                 155
LYS-GLU-TYR-SER-HIS-CYS-ALA-TRP-THR-ILE-VAL-ARG-VAL-GLU-ILE-
AAG GAG TAC AGT CAC TGT GCC TGG ACC ATA GTC AGA GTG GAA ATC
              160                 165                 170
LEU-ARG-ASN-PHE-TYR-PHE-ILE-ASN-ARG-LEU-THR-GLY-TYR-LEU-ARG-
CTA AGG AAC TTT TAC TTC ATT AAC AGA CTT ACA GGT TAC CTC CGA

ASN-TER-
AAC TGA
```

MSCNLLGFLQRSSNFQCQKLLWQLNGRLEYCLKDRMNFDIPEEIKQLQQFQKEDAALTIY
EMLQNIFAIFRQDSSSTGWNETIVENLLANVYHQINHLKTCLEEKLEKEDFTRGKLMSSL
HLKRYYGRILHYLKAKEYSHCAWTIVRVEILRNFYFINRLTGYLRN<

CHART 2

UNITED STATES PATENT AND TRADEMARK OFFICE
CERTIFICATE OF CORRECTION

PATENT NO. : 4,751,077

DATED : June 14, 1988

INVENTOR(S) : Bell, et al.

It is certified that error appears in the above-identified patent and that said Letters Patent is hereby corrected as shown below:

IFNX 804

IFN$\beta$[Tyr$^3$ -> Cys$^3$][Cys$^{17}$ -> Ser$^{17}$][Val$^{101}$ -> Cys$^{101}$]

```
                    5              10                 15
         MET-SER-CYS-ASN-LEU-LEU-GLY-PHE-LEU-GLN-ARG-SER-SER-ASN-PHE-
         ATG AGC TGC AAC TTG CTT GGA TTC CTA CAA AGA AGC AGC AAT TTT 20              25                 30
         GLN-SER-GLN-LYS-LEU-LEU-TRP-GLN-LEU-ASN-GLY-ARG-LEU-GLU-TYR-
         CAG AGT CAG AAG CTC CTG TGG CAA TTG AAT GGG AGG CTT GAA TAC 35              40                 45
         CYS-LEU-LYS-ASP-ARG-MET-ASN-PHE-ASP-ILE-PRO-GLU-GLU-ILE-LYS-
         TGC CTC AAG GAC AGG ATG AAC TTT GAC ATC CCT GAG GAG ATT AAG 50              55                 60
         GLN-LEU-GLN-GLN-PHE-GLN-LYS-GLU-ASP-ALA-ALA-LEU-THR-ILE-TYR-
         CAG CTG CAG CAG TTC CAG AAG GAG GAC GCC GCA TTG ACC ATC TAT 65              70                 75
         GLU-MET-LEU-GLN-ASN-ILE-PHE-ALA-ILE-PHE-ARG-GLN-ASP-SER-SER-
         GAG ATG CTC CAG AAC ATC TTT GCT ATT TTC AGA CAA GAT TCA TCT 80              85                 90
         SER-THR-GLY-TRP-ASN-GLU-THR-ILE-VAL-GLU-ASN-LEU-LEU-ALA-ASN-
         AGC ACT GGC TGG AAT GAG ACT ATT GTT GAG AAC CTC CTG GCT AAT 95             100                105
         VAL-TYR-HIS-GLN-ILE-ASN-HIS-LEU-LYS-THR-CYS-LEU-GLU-GLU-LYS-
         GTC TAT CAT CAG ATA AAC CAT CTG AAG ACA TGC CTG GAA GAA AAA 110             120                125
         LEU-GLU-LYS-GLU-ASP-PHE-THR-ARG-GLY-LYS-LEU-MET-SER-SER-LEU-
         CTG GAG AAA GAA GAT TTC ACC AGG GGA AAA CTC ATG AGC AGT CTG 130             135                140
         HIS-LEU-LYS-ARG-TYR-TYR-GLY-ARG-ILE-LEU-HIS-TYR-LEU-LYS-ALA-
         CAC CTG AAA AGA TAT TAT GGG AGG ATT CTG CAT TAC CTG AAG GCC 145             150                155
         LYS-GLU-TYR-SER-HIS-CYS-ALA-TRP-THR-ILE-VAL-ARG-VAL-GLU-ILE-
         AAG GAG TAC AGT CAC TGT GCC TGG ACC ATA GTC AGA GTG GAA ATC 160             165                170
         LEU-ARG-ASN-PHE-TYR-PHE-ILE-ASN-ARG-LEU-THR-GLY-TYR-LEU-ARG-
         CTA AGG AAC TTT TAC TTC ATT AAC AGA CTT ACA GGT TAC CTC CGA

ASN-TER-
         AAC TGA
```

MSCNLLGFLQRSSNFQSQKLLWQLNGRLEYCLKDRMNFDIPEEIKQLQQFQKEDAALTIY
EMLQNIFAIFRQDSSSTGWNETIVENLLANVYHQINHLKTCLEEKLEKEDFTRGKLMSSL
HLKRYYGRILHYLKAKEYSHCAWTIVRVEILRNFYFINRLTGYLRNK

CHART 3

UNITED STATES PATENT AND TRADEMARK OFFICE
CERTIFICATE OF CORRECTION

PATENT NO. : 4,751,077

DATED : June 14, 1988

INVENTOR(S) : Bell, et al.

It is certified that error appears in the above-identified patent and that said Letters Patent is hereby corrected as shown below:

IFNX815

IFN-β [ser$^2$→cys$^2$][cys$^{17}$→ser$^{17}$]

```
                      5                   10                  15
        MET-CYS-TYR-ASN-LEU-LEU-GLY-PHE-LEU-GLN-ARG-SER-SER-ASN-PHE-
        ATG TGT TAC AAC TTG CTT GGA TTC CTA CAA AGA AGC AGC AAT TTT 20                   25                  30
        GLN-SER-GLN-LYS-LEU-LEU-TRP-GLN-LEU-ASN-GLY-ARG-LEU-GLU-TYR-
        CAG AGT CAG AAG CTC CTG TGG CAA TTG AAT GGG AGG CTT GAA TAC 35                   40                  45
        CYS-LEU-LYS-ASP-ARG-MET-ASN-PHE-ASP-ILE-PRO-GLU-GLU-ILE-LYS-
        TGC CTC AAG GAC AGG ATG AAC TTT GAC ATC CCT GAG GAG ATT AAG 50                   55                  60
        GLN-LEU-GLN-GLN-PHE-GLN-LYS-GLU-ASP-ALA-ALA-LEU-THR-ILE-TYR-
        CAG CTG CAG CAG TTC CAG AAG GAG GAC GCC GCA TTG ACC ATC TAT 65                   70                  75
        GLU-MET-LEU-GLN-ASN-ILE-PHE-ALA-ILE-PHE-ARG-GLN-ASP-SER-SER-
        GAG ATG CTC CAG AAC ATC TTT GCT ATT TTC AGA CAA GAT TCA TCT 80                   85                  90
        SER-THR-GLY-TRP-ASN-GLU-THR-ILE-VAL-GLU-ASN-LEU-LEU-ALA-ASN-
        AGC ACT GGC TGG AAT GAG ACT ATT GTT GAG AAC CTC CTG GCT AAT 95                  100                 105
        VAL-TYR-HIS-GLN-ILE-ASN-HIS-LEU-LYS-THR-VAL-LEU-GLU-GLU-LYS-
        GTC TAT CAT CAG ATA AAC CAT CTG AAG ACA GTC CTG GAA GAA AAA 110                  115                 120
        LEU-GLU-LYS-GLU-ASP-PHE-THR-ARG-GLY-LYS-LEU-MET-SER-SER-LEU-
        CTG GAG AAA GAA GAT TTC ACC AGG GGA AAA CTC ATG AGC AGT CTG 125                  130                 135
        HIS-LEU-LYS-ARG-TYR-TYR-GLY-ARG-ILE-LEU-HIS-TYR-LEU-LYS-ALA-
        CAC CTG AAA AGA TAT TAT GGG AGG ATT CTG CAT TAC CTG AAG GCC 140                  145                 150
        LYS-GLU-TYR-SER-HIS-CYS-ALA-TRP-THR-ILE-VAL-ARG-VAL-GLU-ILE-
        AAG GAG TAC AGT CAC TGT GCC TGG ACC ATA GTC AGA GTG GAA ATC 155                  160                 165
        LEU-ARG-ASN-PHE-TYR-PHE-ILE-ASN-ARG-LEU-THR-GLY-TYR-LEU-ARG-
        CTA AGG AAC TTT TAC TTC ATT AAC AGA CTT ACA GGT TAC CTC CGA

ASN-***-
        AAC TGA 10         20        30        40        50
        MCYNLLGFLQ-RSSNFQSQKL-LWQLNGRLEY-CLKDRMNFDI-PEEIKQLQQF- 60         70        80        90       100
        QKEDAALTIY-EMLQNIFAIF-RQDSSSTGWN-ETIVENLLAN-VYHQINHLKT- 110        120       130       140       150
        VLEEKLEKED-FTRGKLMSSL-HLKRYYGRIL-HYLKAKEYSH-CAWTIVRVEI-

160
        LRNFYFINRL-TGYLRN<         CHART 4
```

UNITED STATES PATENT AND TRADEMARK OFFICE
CERTIFICATE OF CORRECTION

PATENT NO. : 4,751,077

DATED : June 14, 1988

INVENTOR(S) : Bell, et al.

Page 5 of 9

It is certified that error appears in the above-identified patent and that said Letters Patent is hereby corrected as shown below:

IFNX816

IFN-β[ser$^2$→cys$^2$][cys$^{17}$→ser$^{17}$][val$^{101}$→cys$^{101}$]

```
           5                    10                  15
MET-CYS-TYR-ASN-LEU-LEU-GLY-PHE-LEU-GLN-ARG-SER-SER-ASN-PHE-
ATG TGT TAC AAC TTG CTT GGA TTC CTA CAA AGA AGC AGC AAT TTT 20                   25                  30
GLN-SER-GLN-LYS-LEU-LEU-TRP-GLN-LEU-ASN-GLY-ARG-LEU-GLU-TYR-
CAG AGT CAG AAG CTC CTG TGG CAA TTG AAT GGG AGG CTT GAA TAC 35                   40                  45
CYS-LEU-LYS-ASP-ARG-MET-ASN-PHE-ASP-ILE-PRO-GLU-GLU-ILE-LYS-
TGC CTC AAG GAC AGG ATG AAC TTT GAC ATC CCT GAG GAG ATT AAG 50                   55                  60
GLN-LEU-GLN-GLN-PHE-GLN-LYS-GLU-ASP-ALA-ALA-LEU-THR-ILE-TYR-
CAG CTG CAG CAG TTC CAG AAG GAG GAC GCC GCA TTG ACC ATC TAT 65                   70                  75
GLU-MET-LEU-GLN-ASN-ILE-PHE-ALA-ILE-PHE-ARG-GLN-ASP-SER-SER-
GAG ATG CTC CAG AAC ATC TTT GCT ATT TTC AGA CAA GAT TCA TCT 80                   85                  90
SER-THR-GLY-TRP-ASN-GLU-THR-ILE-VAL-GLU-ASN-LEU-LEU-ALA-ASN-
AGC ACT GGC TGG AAT GAG ACT ATT GTT GAG AAC CTC CTG GCT AAT 95                  100                 105
VAL-TYR-HIS-GLN-ILE-ASN-HIS-LEU-LYS-THR-CYS-LEU-GLU-GLU-LYS-
GTC TAT CAT CAG ATA AAC CAT CTG AAG ACA TGC CTG GAA GAA AAA 110                  115                 120
LEU-GLU-LYS-GLU-ASP-PHE-THR-ARG-GLY-LYS-LEU-MET-SER-SER-LEU-
CTG GAG AAA GAA GAT TTC ACC AGG GGA AAA CTC ATG AGC AGT CTG 125                  130                 135
HIS-LEU-LYS-ARG-TYR-TYR-GLY-ARG-ILE-LEU-HIS-TYR-LEU-LYS-ALA-
CAC CTG AAA AGA TAT TAT GGG AGG ATT CTG CAT TAC CTG AAG GCC 140                  145                 150
LYS-GLU-TYR-SER-HIS-CYS-ALA-TRP-THR-ILE-VAL-ARG-VAL-GLU-ILE-
AAG GAG TAC AGT CAC TGT GCC TGG ACC ATA GTC AGA GTG GAA ATC 155                  160                 165
LEU-ARG-ASN-PHE-TYR-PHE-ILE-ASN-ARG-LEU-THR-GLY-TYR-LEU-ARG-
CTA AGG AAC TTT TAC TTC ATT AAC AGA CTT ACA GGT TAC CTC CGA

ASN-***-
AAC TGA 10        20        30        40        50
MCYNLLGFLQ-RSSNFQSQKL-LWQLNGRLEY-CLKDRMNFDI-PEEIKQLQQF- 60        70        80        90       100
QKEDAALTIY-EMLQNIFAIF-RQDSSSTGWN-ETIVENLLAN-VYHQINHLKT- 110       120       130       140       150
CLEEKLEKED-FTRGKLMSSL-HLKRYYGRIL-HYLKAKEYSH-CAWTIVRVEI-

160
LRNFYFINRL-TGYLRN<
```

CHART 5

UNITED STATES PATENT AND TRADEMARK OFFICE
CERTIFICATE OF CORRECTION

PATENT NO. : 4,751,077

DATED : June 14, 1988

INVENTOR(S) : Bell, et al.

It is certified that error appears in the above-identified patent and that said Letters Patent is hereby corrected as shown below:

IFNX817

IFN-β[ser$^2$→cys$^2$]

```
            5                   10                  15
MET-CYS-TYR-ASN-LEU-LEU-GLY-PHE-LEU-GLN-ARG-SER-SER-ASN-PHE-
ATG TGT TAC AAC TTG CTT GGA TTC CTA CAA AGA AGC AGC AAT TTT 20                  25                  30
GLN-CYS-GLN-LYS-LEU-LEU-TRP-GLN-LEU-ASN-GLY-ARG-LEU-GLU-TYR-
CAG TGT CAG AAG CTC CTG TGG CAA TTG AAT GGG AGG CTT GAA TAC 35                  40                  45
CYS-LEU-LYS-ASP-ARG-MET-ASN-PHE-ASP-ILE-PRO-GLU-GLU-ILE-LYS-
TGC CTC AAG GAC AGG ATG AAC TTT GAC ATC CCT GAG GAG ATT AAG 50                  55                  60
GLN-LEU-GLN-GLN-PHE-GLN-LYS-GLU-ASP-ALA-ALA-LEU-THR-ILE-TYR-
CAG CTG CAG CAG TTC CAG AAG GAG GAC GCC GCA TTG ACC ATC TAT 65                  70                  75
GLU-MET-LEU-GLN-ASN-ILE-PHE-ALA-ILE-PHE-ARG-GLN-ASP-SER-SER-
GAG ATG CTC CAG AAC ATC TTT GCT ATT TTC AGA CAA GAT TCA TCT 80                  85                  90
SER-THR-GLY-TRP-ASN-GLU-THR-ILE-VAL-GLU-ASN-LEU-LEU-ALA-ASN-
AGC ACT GGC TGG AAT GAG ACT ATT GTT GAG AAC CTC CTG GCT AAT 95                 100                 105
VAL-TYR-HIS-GLN-ILE-ASN-HIS-LEU-LYS-THR-VAL-LEU-GLU-GLU-LYS-
GTC TAT CAT CAG ATA AAC CAT CTG AAG ACA GTC CTG GAA GAA AAA 110                 115                 120
LEU-GLU-LYS-GLU-ASP-PHE-THR-ARG-GLY-LYS-LEU-MET-SER-SER-LEU-
CTG GAG AAA GAA GAT TTC ACC AGG GGA AAA CTC ATG AGC AGT CTG 125                 130                 135
HIS-LEU-LYS-ARG-TYR-TYR-GLY-ARG-ILE-LEU-HIS-TYR-LEU-LYS-ALA-
CAC CTG AAA AGA TAT TAT GGG AGG ATT CTG CAT TAC CTG AAG GCC 140                 145                 150
LYS-GLU-TYR-SER-HIS-CYS-ALA-TRP-THR-ILE-VAL-ARG-VAL-GLU-ILE-
AAG GAG TAC AGT CAC TGT GCC TGG ACC ATA GTC AGA GTG GAA ATC 155                 160                 165
LEU-ARG-ASN-PHE-TYR-PHE-ILE-ASN-ARG-LEU-THR-GLY-TYR-LEU-ARG-
CTA AGG AAC TTT TAC TTC ATT AAC AGA CTT ACA GGT TAC CTC CGA

ASN-***-
AAC TGA
        10        20        30        40        50
MCYNLLGFLQ-RSSNFQCQKL-LWQLNGRLEY-CLKDRMNFDI-PEEIKQLQQF- 60        70        80        90       100
QKEDAALTIY-EMLQNIFAIF-RQDSSSTGWN-ETIVENLLAN-VYHQINHLKT- 110       120       130       140       150
VLEEKLEKED-FTRGKLMSSL-HLKRYYGRIL-HYLKAKEYSH-CAWTIVRVEI-

160
LRNFYFINRL-TGYLRN(          CHART 6
```

UNITED STATES PATENT AND TRADEMARK OFFICE
CERTIFICATE OF CORRECTION

PATENT NO. : 4,751,077

DATED : June 14, 1988

INVENTOR(S) : Bell, et al.

Page 7 of 9

It is certified that error appears in the above-identified patent and that said Letters Patent is hereby corrected as shown below:

IFNX818

IFN-$\beta$[ser$^2$->cys$^2$][val$^{101}$->cys$^{101}$]

```
               5                   10                  15
MET-CYS-TYR-ASN-LEU-LEU-GLY-PHE-LEU-GLN-ARG-SER-SER-ASN-PHE-
ATG TGT TAC AAC TTG CTT GGA TTC CTA CAA AGA AGC AGC AAT TTT 20                  25                  30
GLN-CYS-GLN-LYS-LEU-LEU-TRP-GLN-LEU-ASN-GLY-ARG-LEU-GLU-TYR-
CAG TGT CAG AAG CTC CTG TGG CAA TTG AAT GGG AGG CTT GAA TAC 35                  40                  45
CYS-LEU-LYS-ASP-ARG-MET-ASN-PHE-ASP-ILE-PRO-GLU-GLU-ILE-LYS-
TGC CTC AAG GAC AGG ATG AAC TTT GAC ATC CCT GAG GAG ATT AAG 50                  55                  60
GLN-LEU-GLN-GLN-PHE-GLN-LYS-GLU-ASP-ALA-ALA-LEU-THR-ILE-TYR-
CAG CTG CAG CAG TTC CAG AAG GAG GAC GCC GCA TTG ACC ATC TAT 65                  70                  75
GLU-MET-LEU-GLN-ASN-ILE-PHE-ALA-ILE-PHE-ARG-GLN-ASP-SER-SER-
GAG ATG CTC CAG AAC ATC TTT GCT ATT TTC AGA CAA GAT TCA TCT 80                  85                  90
SER-THR-GLY-TRP-ASN-GLU-THR-ILE-VAL-GLU-ASN-LEU-LEU-ALA-ASN-
AGC ACT GGC TGG AAT GAG ACT ATT GTT GAG AAC CTC CTG GCT AAT 95                 100                 105
VAL-TYR-HIS-GLN-ILE-ASN-HIS-LEU-LYS-THR-CYS-LEU-GLU-GLU-LYS-
GTC TAT CAT CAG ATA AAC CAT CTG AAG ACA TGC CTG GAA GAA AAA 110                 115                 120
LEU-GLU-LYS-GLU-ASP-PHE-THR-ARG-GLY-LYS-LEU-MET-SER-SER-LEU-
CTG GAG AAA GAA GAT TTC ACC AGG GGA AAA CTC ATG AGC AGT CTG 125                 130                 135
HIS-LEU-LYS-ARG-TYR-TYR-GLY-ARG-ILE-LEU-HIS-TYR-LEU-LYS-ALA-
CAC CTG AAA AGA TAT TAT GGG AGG ATT CTG CAT TAC CTG AAG GCC 140                 145                 150
LYS-GLU-TYR-SER-HIS-CYS-ALA-TRP-THR-ILE-VAL-ARG-VAL-GLU-ILE-
AAG GAG TAC AGT CAC TGT GCC TGG ACC ATA GTC AGA GTG GAA ATC 155                 160                 165
LEU-ARG-ASN-PHE-TYR-PHE-ILE-ASN-ARG-LEU-THR-GLY-TYR-LEU-ARG-
CTA AGG AAC TTT TAC TTC ATT AAC AGA CTT ACA GGT TAC CTC CGA

ASN-***-
AAC TGA 10        20        30        40        50
MCYNLLGFLQ-RSSNFQCQKL-LWQLNGRLEY-CLKDRMNFDI-PEEIKQLQQF- 60        70        80        90       100
QKEDAALTIY-EMLQNIFAIF-RQDSSSTGWN-ETIVENLLAN-VYHQINHLKT- 110       120       130       140       150
CLEEKLEKED-FTRGKLMSSL-HLKRYYGRIL-HYLKAKEYSH-CAWTIVRVEI-

160
LRNFYFINRL-TGYLRN<
```

CHART 7

UNITED STATES PATENT AND TRADEMARK OFFICE
CERTIFICATE OF CORRECTION

PATENT NO. : 4,751,077

DATED : June 14, 1988

INVENTOR(S) : Bell, et al.

It is certified that error appears in the above-identified patent and that said Letters Patent is hereby corrected as shown below:

IFNX457

IFN-β[IFN-β2-7->IFN-α$_2$1-5][cys$^{16}$->ser$^{16}$][val$^{188}$->cys$^{188}$]

```
                      5                    10                   15
        MET-CYS-ASP-LEU-PRO-GLN-PHE-LEU-GLN-ARG-SER-SER-ASN-PHE-GLN-
        ATG TGC GAC TTA CCA CAA TTC CTA CAA AGA AGC AGC AAT TTT CAG 20                    25                   30
        SER-GLN-LYS-LEU-LEU-TRP-GLN-LEU-ASN-GLY-ARG-LEU-GLU-TYR-CYS-
        TCT CAG AAG CTC CTG TGG CAA TTG AAT GGG AGG CTT GAA TAT TGC 35                    40                   45
        LEU-LYS-ASP-ARG-MET-ASN-PHE-ASP-ILE-PRO-GLU-GLU-ILE-LYS-GLN-
        CTC AAG GAC AGG ATG AAC TTT GAC ATC CCT GAG GAG ATT AAG CAG 50                    55                   60
        LEU-GLN-GLN-PHE-GLN-LYS-GLU-ASP-ALA-ALA-LEU-THR-ILE-TYR-GLU-
        CTG CAG CAG TTC CAG AAG GAG GAC GCC GCA TTG ACC ATC TAT GAG 65                    70                   75
        MET-LEU-GLN-ASN-ILE-PHE-ALA-ILE-PHE-ARG-GLN-ASP-SER-SER-SER-
        ATG CTC CAG AAC ATC TTT GCT ATT TTC AGA CAA GAT TCA TCT AGC 80                    85                   90
        THR-GLY-TRP-ASN-GLU-THR-ILE-VAL-GLU-ASN-LEU-LEU-ALA-ASN-VAL-
        ACT GGC TGG AAT GAG ACT ATT GTT GAG AAC CTC CTG GCT AAT GTC 95                   100                  105
        TYR-HIS-GLN-ILE-ASN-HIS-LEU-LYS-THR-VAL-LEU-GLU-GLU-LYS-LEU-
        TAT CAT CAG ATA AAC CAT CTG AAG ACA GTC CTG GAA GAA AAA CTG 110                   115                  120
        GLU-LYS-GLU-ASP-PHE-THR-ARG-GLY-LYS-LEU-MET-SER-SER-LEU-HIS-
        GAG AAA GAA GAT TTC ACC AGG GGA AAA CTC ATG AGC AGT CTG CAC 125                   130                  135
        LEU-LYS-ARG-TYR-TYR-GLY-ARG-ILE-LEU-HIS-TYR-LEU-LYS-ALA-LYS-
        CTG AAA AGA TAT TAT GGG AGG ATT CTG CAT TAC CTG AAG GCC AAG 140                   145                  150
        GLU-TYR-SER-HIS-CYS-ALA-TRP-THR-ILE-VAL-ARG-VAL-GLU-ILE-LEU-
        GAG TAC AGT CAC TGT GCC TGG ACC ATA GTC AGA GTG GAA ATC CTA 155                   160                  165
        ARG-ASN-PHE-TYR-PHE-ILE-ASN-ARG-LEU-THR-GLY-TYR-LEU-ARG-ASN-
        AGG AAC TTT TAC TTC ATT AAC AGA CTT ACA GGT TAC CTC CGA AAC

***-
        TGA
              10        20        30        40        50
        MCDLPQFLQR-SSNFQSQKLL-WQLNGRLEYC-LKDRMNFDIP-EEIKQLQQFQ- 60        70·       80        90       100
        KEDAALTIYE-MLQNIFAIFR-QDSSSTGWNE-TIVENLLANV-YHQINHLKTV- 110       120       130       140       150
        LEEKLEKEDF-TRGKLMSSLH-LKRYYGRILH-YLKAKEYSHC-AWTIVRVEIL-

160
        RNFYFINRLT-GYLRNK
```

CHART 8

UNITED STATES PATENT AND TRADEMARK OFFICE
CERTIFICATE OF CORRECTION

PATENT NO. : 4,751,077

DATED : June 14, 1988

INVENTOR(S) : Bell, et al.

It is certified that error appears in the above-identified patent and that said Letters Patent is hereby corrected as shown below:

Column 4, line 23, reading "HuIFN-62" should read -- HuIFN-$\beta$ --.

Column 8, line 25, reading "0 2mM" should read -- 0.2 mM --.

Column 13, line 27, reading "HuIFN-X8041" should read -- HuIFN-X804 --.

Signed and Sealed this

Tenth Day of April, 1990

Attest:

HARRY F. MANBECK, JR.

*Attesting Officer*   *Commissioner of Patents and Trademarks*